US012616982B2

(12) United States Patent
Ciavarella et al.

(10) Patent No.: US 12,616,982 B2
(45) Date of Patent: May 5, 2026

(54) SPRAYERS HAVING INCREASED FINE DROPLET TRANSFER EFFICIENCY

(71) Applicant: GOJO Industries, Inc., Akron, OH (US)

(72) Inventors: Nick E. Ciavarella, Seven Hills, OH (US); Mark S. Kacik, Avon Lake, OH (US)

(73) Assignee: GOJO Industries, Inc., Akron, OH (US)

( * ) Notice: Subject to any disclaimer, the term of this patent is extended or adjusted under 35 U.S.C. 154(b) by 564 days.

(21) Appl. No.: 17/839,556

(22) Filed: Jun. 14, 2022

(65) Prior Publication Data

US 2022/0401970 A1      Dec. 22, 2022

Related U.S. Application Data

(60) Provisional application No. 63/211,593, filed on Jun. 17, 2021.

(51) Int. Cl.
| | |
|---|---|
| *B05B 1/10* | (2006.01) |
| *A61L 2/22* | (2006.01) |
| *B05B 7/04* | (2006.01) |
| *B05B 11/00* | (2023.01) |
| *B05B 11/10* | (2023.01) |

(52) U.S. Cl.
CPC ..................................... *B05B 1/10* (2013.01);
*A61L 2/22* (2013.01); *B05B 7/0416* (2013.01);
*B05B 11/0037* (2013.01); *B05B 11/1087*
(2023.01); *A61L 2202/15* (2013.01); *A61L*
*2202/18* (2013.01)

(58) Field of Classification Search
CPC ..... B05B 1/10; B05B 7/0416; B05B 11/0037;
B05B 11/1087; B05B 1/28; B05B 1/3402;
B05B 7/0075; B05B 7/0087; B05B 7/067;
B05B 7/0815; B05B 7/2402; B05B 12/18;
B05B 7/0081; A61L 2/22; A61L 2202/15;
A61L 2202/18; A61L 2/18
See application file for complete search history.

(56) References Cited

U.S. PATENT DOCUMENTS

| | | | | |
|---|---|---|---|---|
| 4,779,805 A | * | 10/1988 | Jackson | .............. A01M 7/0089 |
| | | | | 239/296 |
| 5,224,651 A | | 7/1993 | Stahl | |
| 2020/0054000 A1 | | 2/2020 | Zwahlen et al. | |

FOREIGN PATENT DOCUMENTS

| | | | | |
|---|---|---|---|---|
| CN | 105234017 A | * | 1/2016 | ............. B05B 12/18 |
| FR | 2457130 A1 | | 12/1980 | |

OTHER PUBLICATIONS

International Search Report and Written Opinion from PCT/US2022/033329 dated Oct. 4, 2022.

* cited by examiner

*Primary Examiner* — Qingzhang Zhou

(74) *Attorney, Agent, or Firm* — Calfee, Halter & Griswold LLP

(57)      ABSTRACT

A fine particle sprayer including a nozzle for dispersing a liquid disinfectant into a spray plume of droplets and a means for directing pressurized air below the spray plume to increase droplet transfer efficiency, and above and around the spray plume to prevent errant droplets from drifting toward an operator. A sprayer system includes a sprayer, a housing, and a blower that may be removably attached to the sprayer for generating an air stream below the droplets to improve droplet transfer efficiency.

8 Claims, 8 Drawing Sheets

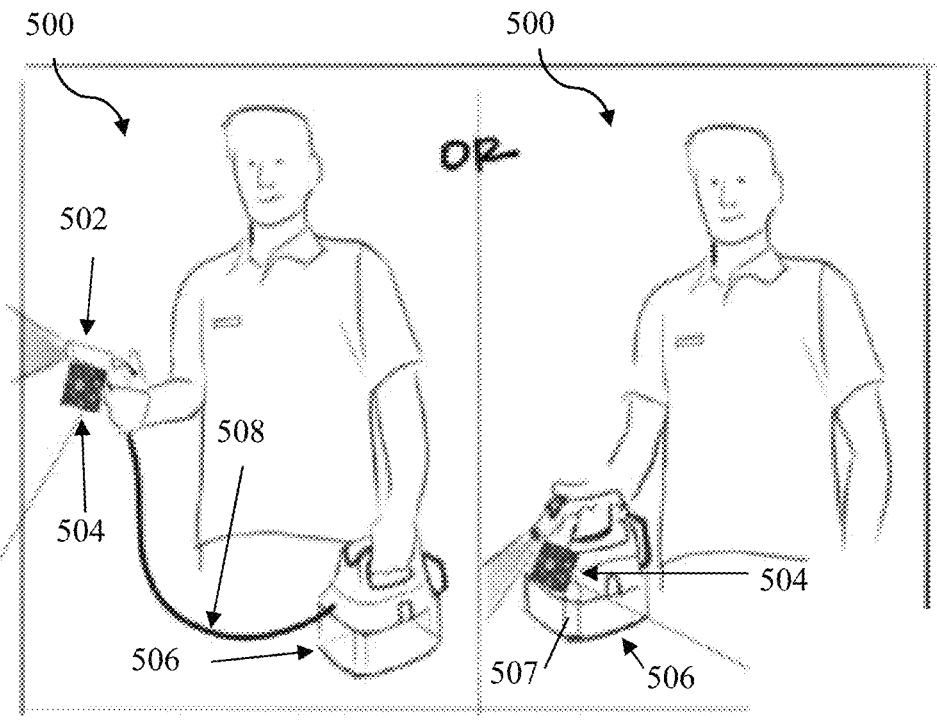
FIG. 11          FIG. 12
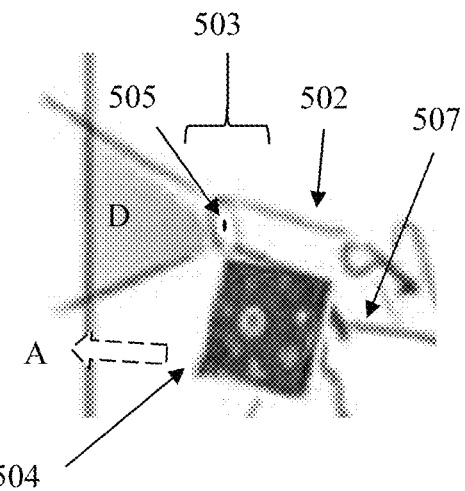
FIG. 13
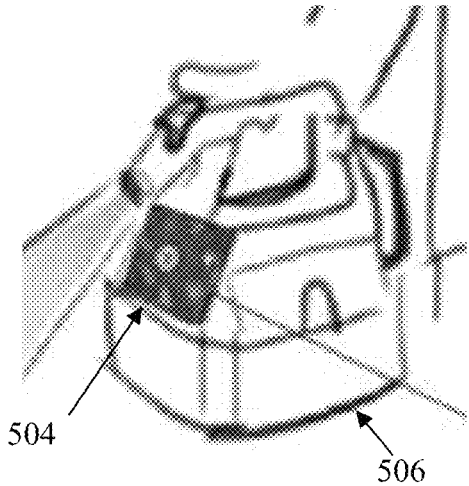
FIG. 14

SPRAYERS HAVING INCREASED FINE DROPLET TRANSFER EFFICIENCY

RELATED APPLICATIONS

The present invention claims priority to, and the benefits of, U.S. Provisional Patent Application Ser. No. 63/211,593, filed on Jun. 17, 2021 and titled SPRAYERS HAVING INCREASED FINE DROPLET TRANSFER EFFICIENCY, which is incorporated herein by reference in its entirety.

TECHNICAL FIELD

The present invention relates generally to fine particulate sprayers having increased fine droplet or aerosol droplet transfer efficiency, and more particularly, to disinfectant sprayers and sprayer systems that are configured to use directed air streams to increase droplet transfer efficiency.

BACKGROUND OF THE INVENTION

Disinfectant sprayers are utilized to sanitize surfaces (e.g., tabletops, chairs, handles, equipment and the like) by dispensing a liquid disinfectant comprised of a mist of fine fluid particles and fine droplets onto the surface for killing bacteria, viruses, and other germs that may be on the surface. Such sprayers commonly utilize a pump for driving a liquid disinfectant from a fluid reservoir to an applicator (e.g., a wand). Such sprayers also typically include a nozzle that is configured to atomize the liquid disinfectant into a spray plume or mist of droplets that are directed toward a target surface. When spraying in close proximity to a target surface, droplets discharged from the sprayer may be carried off target by local recirculating currents and vortices in the flow, and/or bounce back from the surface, thereby back from the surface, thereby exposing an operator to volatile organic compounds (VOCs) associated with chemicals used in the liquid disinfectant formula. When operating at a greater distance from the target surface, in addition to being carried off target by local recirculating currents and vortices, some droplets may fall to a ground surface, thereby decreasing the droplet transfer efficiency to the desired surface.

High pressure, air assisted sprayers have been used for increasing droplet transfer efficiency by directing a high-pressure air stream into the spray plume for projecting the droplets toward the target surface. However, high-pressure, air assisted sprayers are not suitable for certain applications, such as, for example, those that utilize a liquid disinfectant that is susceptible to drying out (e.g., alcohol-based disinfectants). In addition, imparting high-pressure air directly into the spray plume may diminish a droplet's dwell time on the target surface, respectively, by, for example, reducing the size of the droplet (due to evaporation) before it reaches the target surface and is not practical in office environments due to noise, capacity etc. Additionally, in some applications, operating at a greater distance from a target surface may cause some droplets to become errant and drift toward an operator, such as, for example, when a smaller, lighter droplet becomes mobilized by vortices or eddies that are created by the interaction between the spray plume and the surrounding, stagnant air and/or the front end of a sprayer.

Often, an operator will utilize one sprayer for spraying surfaces in close proximity (e.g., tabletops, poles, chairs), and a different sprayer to spray down larger surfaces (e.g., a vertical wall) from a greater distance. Changing out sprayers creates downtime and increases equipment carrying costs, i.e., maintaining two sprayers versus one. For example, a janitorial staff member may have to walk to a remote storage area (e.g., a closet) in a hospital, school, or other large institution to obtain a sprayer that is suitable for the particular application. Applicant has appreciated the need for a portable and cost-effective means of utilizing a sprayer that is versatile for a variety of applications, increases droplet transfer efficiency, and minimizes the possibility of VOC exposure to an operator.

SUMMARY

Exemplary embodiments of fine droplet sprayers are disclosed herein. An exemplary fine droplet sprayer for spraying a disinfectant onto a surface includes a reservoir for holding a disinfectant fluid, a pump for pumping the disinfectant fluid an applicator and a fluid dispensation conduit extending from the pump to the applicator. The applicator includes a housing, a liquid outlet nozzle, an air moving device, and a first air passageway from the air moving device to a first air outlet. The first air outlet is at least partially cylindrical. Air flowing from the air moving device to the first air outlet forms at least a partial cylindrical air stream. The at least a partial cylindrical air stream exits the first air outlet at a first speed. The at least partial cylindrical air stream is located around a periphery of the housing; and the at least partial cylindrical air stream is located away from the liquid outlet nozzle, such that the at least partial cylindrical air stream does not contact the fluid at the time the fluid is pumped out of the liquid outlet nozzle.

Another fine droplet sprayer for spraying a disinfectant onto a surface includes a reservoir for holding a disinfectant fluid, a pump for pumping the disinfectant fluid, an applicator and a fluid dispensation conduit extending from the pump to a liquid outlet nozzle. The applicator includes a housing, a first air moving device, a first air passageway from the first air moving device to a first air outlet, a second air moving device and a second air passageway from the second air moving device to a second air outlet. The second air outlet at least partially surrounds the liquid outlet nozzle. The second air outlet is located between the first air outlet and the liquid outlet nozzle. The first air moving device moves air out of the first air outlet at a first velocity and the second air moving device moves air out of the second outlet at a second velocity.

Another fine particle sprayer for dispensing a disinfectant onto a surface includes a pump, a container for holding liquid, and an applicator. The applicator has a body having a first end and a second end, wherein the first end includes an annular opening, and wherein the second end includes a grip member extending therefrom. The body comprises an annular channel that is configured to supply pressurized air through the annular opening. The body further comprises a liquid line for supplying a pressurized liquid pumped from the container to a nozzle disposed at the first end. The nozzle facilitates the dispersion of the pressurized liquid into droplets and directs the droplets toward a target. The first end of the sprayer further comprises a baffle having an outer surface comprised of a frustoconical-shaped first portion and a cylindrical-shaped second portion, wherein the first portion and the second portion cooperate to induce the pressurized air exiting the annular opening to pass over the first and second portions and form a substantially horizontal, coaxial air stream around the droplets exiting nozzle.

Another exemplary fine particle sprayer for dispensing a disinfectant onto a surface includes a pump, a container for holding liquid and an applicator. The applicator includes a body having a first end and a second end, wherein the first end includes an annular opening, and wherein the second end includes a handle extending therefrom. The body comprises a blower and an annular channel that is configured to supply pressurized air through the annular opening. The body further includes a liquid line for supplying a pressurized liquid from the pump to a nozzle disposed at the first end. The nozzle facilitates the dispersion of the pressurized liquid into droplets and directs the droplets toward a surface, and the first end of the sprayer further comprises a baffle having a convex-shaped outer surface that induces the pressurized air from the blower exiting the annular opening to pass over the outer surface and form a substantially horizontal, coaxial air stream around the droplets exiting nozzle.

Another exemplary fine particle sprayer applicator for dispensing a disinfectant onto a surface includes a body having a first end and a second end, wherein the first end includes an annular opening, and wherein the second end includes a handle extending therefrom. The body comprises an annular channel that is configured to supply pressurized air through the annular opening. The body further comprises a fluid line for supplying a pressurized fluid to a nozzle disposed at the first end. The nozzle facilitates the dispersion of the pressurized fluid into droplets and directs the droplets toward a surface and the first end of the sprayer further comprises a baffle having an outer surface that induces the pressurized air exiting the annular opening to pass over the outer surface and form a substantially horizontal, coaxial air stream around the droplets. The sprayer further includes means for adjusting the velocity of the coaxial air stream relative to the velocity of the droplets such that the velocity of the coaxial air stream matches the velocity of the droplets.

Another fine particle sprayer applicator for dispensing a disinfectant onto a surface includes a body having a first end and a second end, wherein the first end includes an annular opening, and wherein the second end includes a handle extending therefrom. The body includes an annular channel that is configured to supply pressurized air through the annular opening. The body further comprises a fluid line for supplying a pressurized fluid to a nozzle disposed at the first end. The nozzle facilitates the dispersion of the pressurized fluid into droplets and directs the droplets toward a surface. The first end of the sprayer further comprises a baffle having an outer surface that induces the pressurized air exiting the annular opening to pass over the outer surface and form a substantially horizontal, coaxial air stream around the droplets and an annular lip is disposed around the annular opening, the annular lip extending outward horizontally and configured to reduce vortices created by the interaction of the coaxial air stream and the atmospheric air.

Another exemplary fine particle sprayer applicator for dispensing a disinfectant onto a surface, includes a body having a first end and a second end, wherein the first end includes an annular opening, and wherein the second end includes a handle extending therefrom. The body comprises an annular channel that is configured to supply pressurized air through the annular opening. The body further comprises a fluid line for supplying a pressurized fluid to a nozzle disposed at the first end. The nozzle facilitates the dispersion of the pressurized fluid into droplets and directs the droplets toward a surface. The first end of the sprayer further comprises a baffle having an outer surface that induces the pressurized air exiting the annular opening to pass over the outer surface and form a substantially horizontal, coaxial air stream around the droplets and the baffle comprises a central channel that is configured to supply pressurized air through an opening formed in the baffle to form an axial air stream for projecting droplets toward the target surface.

Another fine particle sprayer applicator for dispensing a disinfectant onto a surface includes a body having a first end and a second end, wherein the first end includes an annular opening. The body comprises an annular channel that is configured to supply pressurized air through the annular opening. The body further comprises a fluid line for supplying a pressurized fluid to a nozzle disposed at the first end. The nozzle facilitates the dispersion of the pressurized fluid into droplets and directs the droplets toward a surface, and an annular lip is disposed around the annular opening, the annular lip extending outward horizontally and configured to reduce vortices created by the interaction of the coaxial air stream and the atmospheric air.

Another exemplary embodiment of a fine particle applicator for dispensing a disinfectant onto a surface includes a body having a first end and a second end, wherein the first end includes an annular opening, and wherein the second end includes a handle extending therefrom. The body comprises an annular channel that is configured to supply a pressurized air stream through the annular opening. The body further comprises a fluid line for supplying a pressurized fluid to a nozzle disposed at the first end. The nozzle facilitates the dispersion of the pressurized fluid into droplets and directs the droplets toward a surface. The first end of the sprayer further comprises a baffle having an inner surface that induces the pressurized air stream passing through the annular channel to wrap around the inner surface and form a substantially horizontal, coaxial air stream around the droplets, and a blower is disposed at the second end of the body, the blower being configured to generate the pressurized air stream.

Another exemplary embodiment of a fine particle sprayer applicator for dispensing a disinfectant onto a surface includes a body having a first end and a second end, wherein the first end includes an annular opening. The body comprises an annular channel that is configured to supply a pressurized air stream through the annular opening. The body further comprises a fluid line for supplying a pressurized fluid to a nozzle disposed at the first end. The nozzle facilitates the dispersion of the pressurized fluid into droplets and directs the droplets toward a surface. The first end of the sprayer further includes a baffle having an inner surface that induces the pressurized air stream passing through the annular channel to wrap around the inner surface and form a substantially horizontal, coaxial air stream around the droplets. A blower is disposed at the second end of the body, the blower being configured to generate the pressurized air stream. This exemplary embodiment includes means for adjusting the velocity of the pressurized air stream such that that the velocity of the coaxial air stream is equal to the velocity of the droplets exiting the nozzle.

Another exemplary embodiment of a fine particle sprayer applicator for dispensing a disinfectant onto a surface includes a body having a first end and a second end, wherein the first end includes an annular opening. The body comprises an annular channel that is configured to supply a pressurized air stream through the annular opening. The body further includes a fluid line for supplying a pressurized fluid to a nozzle disposed at the first end. The nozzle facilitates the dispersion of the pressurized fluid into droplets and directs the droplets toward a surface. The first end of the sprayer further includes a baffle having a convex-shaped inner surface that induces the pressurized air stream passing through the annular channel to wrap around the inner surface and form a substantially horizontal, coaxial air stream around the droplets, and a blower is disposed at the second end of the body, the blower being configured to generate the pressurized air stream.

Another exemplary fine particle sprayer applicator for dispensing a disinfectant onto a surface includes a means for adjusting the velocity of the second pressurized air stream such that that the velocity of the second pressurized air stream is equal to the velocity of the droplets exiting the nozzle.

Another exemplary fine particle sprayer applicator for dispensing a disinfectant onto a surface includes a means for adjusting the velocity of the pressurized fluid such that that the velocity of the second pressurized air stream is substantially equal to or exceeds the velocity of the droplets exiting the nozzle.

Another exemplary fine particle sprayer applicator for dispensing a disinfectant onto a surface includes means for adjusting the velocity of the first pressurized air stream and the second pressurized air stream such that that the velocity of the first pressurized air stream and the velocity of the second pressurized air stream is equal to the velocity of the droplets exiting the nozzle.

Another exemplary fine particle sprayer applicator for dispensing a disinfectant onto a surface includes means for adjusting the velocity of the pressurized air such that that the velocity of the pressurized air stream is equal to the velocity of the droplets exiting the nozzle.

Another exemplary fine particle sprayer applicator for dispensing a disinfectant onto a surface includes a means for adjusting the velocity of the lower air stream relative to the velocity of the droplets exiting the nozzle.

BRIEF DESCRIPTION OF THE DRAWINGS

These and other features and advantages of the present invention will become better understood with regard to the following description and accompanying drawings in which:

FIG. 11 illustrates a perspective view of a sprayer system with a blower attached to a sprayer according to an exemplary embodiment;

FIG. 12 illustrates a perspective view of the sprayer system of FIG. 11 with the blower attached to a housing according to an exemplary embodiment;

FIG. 13 is a close-up, perspective view of a blower attached to the front end of a sprayer according to an exemplary embodiment; and FIG. 14 is a close-up, perspective view of a blower attached to a housing according to an exemplary embodiment.

DETAILED DESCRIPTION

The following includes definitions of exemplary terms used throughout the disclosure. Both singular and plural forms of all terms fall within each meaning. Except where noted otherwise, capitalized and non-capitalized forms of all terms fall within each meaning:

"Droplet transfer efficiency" is defined as the percentage of material (e.g., liquid disinfectant) projected from the sprayer that contacts a target surface. Any values identified in the detailed description are exemplary and are determined as needed for a particular design. Accordingly, the inventive concepts disclosed and claimed herein are not limited to the particular values or ranges of values used to describe the embodiments disclosed herein unless expressly set forth therein. Moreover, the detailed description describes exemplary embodiments of the invention and is not intended to limit the scope of the claims in any way. Indeed, the invention is broader than and unlimited by the exemplary embodiments, and the terms used in the claims have their full ordinary meaning. Features and components of one exemplary embodiment may be incorporated into the other exemplary embodiments. Inventions within the scope of this application may include additional features, or may have less features, than those shown in the exemplary embodiments.

Figure 1:
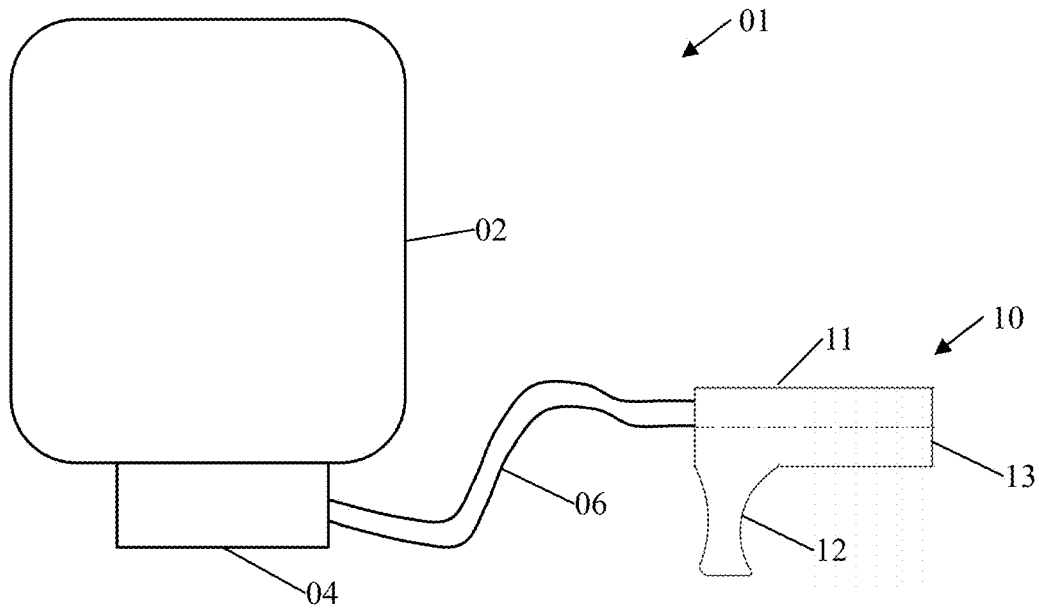
FIG. 1 is a schematic view of an exemplary embodiment of a fine droplet sprayer system.

FIG. 1 illustrates an exemplary embodiment of a sprayer system 01. Exemplary sprayer system 01 includes tank 02 or reservoir for holding a cleaning and/or disinfecting solution, a pumping system 04, a fluid hose 06, and an applicator 10. Pumping system 04 includes a liquid pump (not shown) for pumping liquid from tank 02 to applicator 10 through fluid hose 06. The liquid pump (not shown) may be a manual liquid pump or an electric pump. If the pump is an electric pump, pumping system 04 may include a power source (not shown), such as, for example, one or more batteries. In addition, pumping system 04 may contain an air pump or blower (not shown) for pumping air. In such embodiments, there may optionally be two fluid hoses, one for pumping liquid and one for pumping air. In some embodiments, pumping system 04 includes a power source for powering a blower, in or on, applicator 10 and one or more wires may be routed from pumping system 04 to applicator 10 along fluid hose 06.

Applicator 10 includes an applicator body 11 having a handle 12 and an outlet 13. Exemplary sprayer system 01 is configured to dispense a liquid disinfectant comprised of a mist of fluid particles or droplets (i.e., a spray plume) from the outlet 13 toward a target surface, such as, for example, tabletops, chairs, poles, handles, walls, floors and the like.

Figure 2:
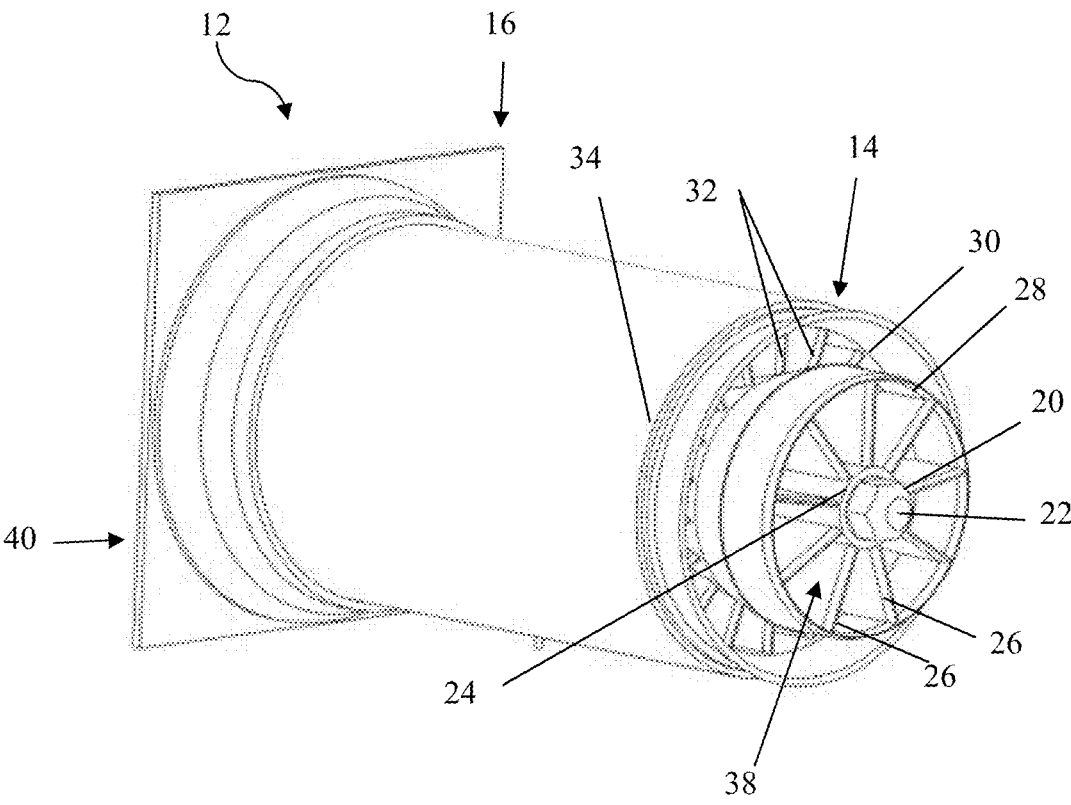
FIG. 2 illustrates a perspective view of an applicator according to an exemplary embodiment.

FIG. 2 illustrates an exemplary embodiment of an applicator 12 for use in a sprayer system (not shown). The sprayer system may be similar to the sprayer system of FIG. 1 or may be any type of system that is configured to provide pressurized fluid to applicator 12. In this exemplary embodiment, applicator 12 includes an air inlet 16 and an outlet 14. The outlet 14 of the applicator 12 may include a spray nozzle 20 that is configured to disperse a liquid disinfectant in the form of droplets directed toward a target surface, e.g., via atomization of the liquid disinfectant.

The spray nozzle 20 may take any suitable form, such as, for example, a full-cone nozzle (e.g., conventional type, swirl chamber type, air induction type, impinging jet type), a fluidic nozzle, an ultrasonic nozzle, Orifice, Pre-orifice type, dynamic impulse driven, deflection type, rotary disc, flat spray, coanda effect, turbulent chamber and the like. In some embodiments, multiple spray nozzles may be used, such as, for example, two or more small orifice type spray nozzles aimed in different directions. In some embodiments, the spray nozzle 20 may include an orifice 22 that is sized and dimensioned to generate a predetermined droplet velocity, as described in greater detail below. In some embodiments, the spray nozzle 20 may include an upstream pre-orifice and a downstream orifice (not shown) such that a pressure reducing chamber is formed within the nozzle for creating larger-sized droplets and minimizing droplet drift, e.g., for reducing VOC exposure associated with lighter, smaller droplets drifting toward a user. In some exemplary embodiments, the spray nozzle 20 produces a droplet size between 10-1000 microns. In some embodiments, producing a larger droplet size is desirable to ensure that the droplets will have enough kinetic energy to make it to a target surface and not be carried away by aerodynamic forces as the air current changes direction. Moreover, in such embodiments, producing a larger droplet size may be beneficial for increasing a droplet's dwell time on the target surface before it evaporates, e.g., for enabling an adequate dwell time on the surface to kill a target organism type.

Still referring to FIG. 2, the exemplary spray nozzle 20 is optionally disposed in a central hub 24 that is supported by a plurality of radial fins 26 that are affixed to a baffle 28, as discussed in greater detail below. In some embodiments, the applicator 12 may include an annular opening 30 that is defined by the space between the baffle 28 and an outer circumferential wall 34 of the applicator 12. In some embodiments, the baffle 28 is connected to the outer circumferential wall 34 via a plurality of radial ribs 32.

Figure 3:
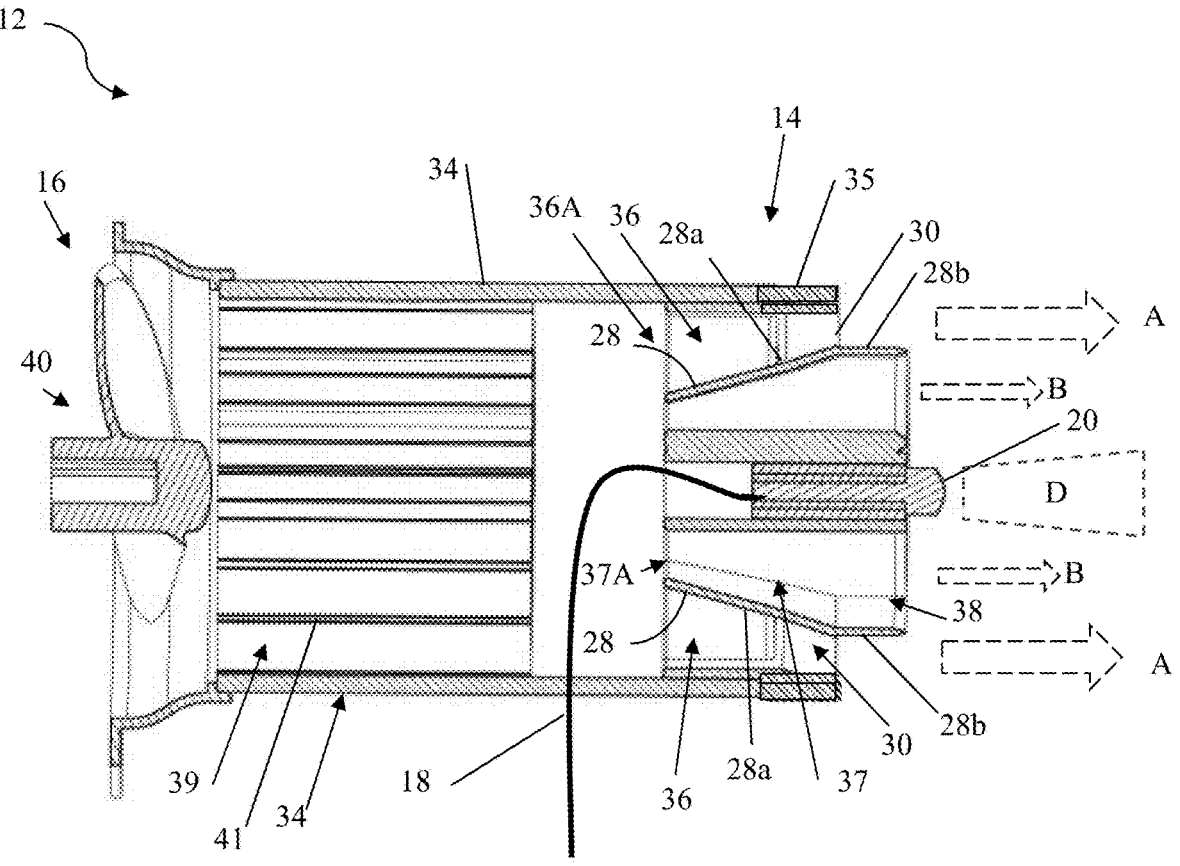
FIG. 3 illustrates a cross-sectional view of the applicator of FIG. 2.

Referring to FIG. 3, in exemplary embodiments, a fluid line 18 is connected to the spray nozzle 20 for supplying a pressurized fluid, e.g. a pressurized liquid disinfectant to the spray nozzle 20. While the illustrated embodiment depicts the fluid line 18 entering the applicator 12 through the circumferential wall 34, it should be appreciated that the fluid line 18 may be introduced into the applicator 12 at other entry points, e.g., through a rear portion of the applicator 12, through the handle (not shown) and into the applicator 12, etc. In exemplary embodiments, the applicator 12 includes an annular channel 36 that is configured to supply pressurized air through the annular opening 30, respectively, for creating a substantially horizontal, coaxial air stream A around a spray plume of droplets D emitted by the spray nozzle 20. In this exemplary embodiment, cross-sectional area of annular channel 36 reduces as it progresses from the inlet 36A to the annular opening 30. Accordingly, the velocity of the air is increased as it passes through annular channel 36.

In some embodiments, the baffle 28 includes an optional outer surface comprising a frustoconical-shaped first portion 28a and a cylindrical-shaped second portion 28b that are configured to induce pressurized air passing through the annular channel 36 to wrap around the first portion 28a and the second portion 28b, respectively, to form the coaxial air stream A. More specifically, pressurized air passing through the annular channel 36 wraps around the first portion 28a and the second portion 28b of the baffle 28 via the Coanda effect, i.e., the tendency of a fluid jet to stay attached to a curved surface. However, it should be understood that the first and the second portions 28a and 28b can be formed to define other shapes, such as, for example, a single, convex-shaped portion (not shown). In this manner, it is contemplated that other configurations are also contemplated for creating the coaxial air stream A via the Coanda effect.

Still referring to FIG. 3, in this exemplary embodiment, the coaxial air stream A is intentionally formed around the air that surrounds the spray plume of droplets D emitted by the nozzle to prevent and/or reduce droplets from intermixing with the coaxial air stream A. The air that surrounds the spray plume of droplets D may be relatively stagnant air, or may be moving air. In this exemplary embodiment, if it is desired to have stagnant air surrounding the plume of droplets, the opening 37A of central channel 37 may be sealed off to prevent and/or limit and/or reduce the air flow therethrough.

This feature is particularly useful in some embodiments for preserving the liquidity of the droplets, which may not occur in situations where high-pressure air is imparted directly into the spray plume. In addition, the coaxial air stream A reduces vortices that may otherwise be created based on the interaction of the spray plume and the surrounding stagnant air, or an air flow having a lower velocity than coaxial air stream A. In this manner, the coaxial air stream A may help concentrate the spray plume such that it is more focused and directed, thereby enabling more uniform coverage on the target surface. Furthermore, by generating a more focused spray plume, operating and aiming the sprayer is made easier.

Preferably, the spray angle of the nozzle should be at an angle that is greater than a minimum angle, such as 0 degrees but less than a maximum angle. In some embodiments, the minimum angle is greater than 1 degree. In some embodiments, the minimum angle is greater than 2 degrees. In some embodiments, the minimum angle is greater than 3 degrees. In some embodiments, the minimum angle is greater than 4 degrees. In some embodiments, the minimum angle is greater than 5 degrees. The maximum angle is an angle in which the droplets will likely penetrate through the coaxial air stream. In some embodiments, the maximum angle is less than 45 degrees. In some embodiments, the maximum angle is less than 40 degrees. In some embodiments, the maximum angle is less than 35 degrees. In some embodiments, the maximum angle is less than 30 degrees. In some embodiments, the maximum angle is less than 25 degrees. In some embodiments, the maximum angle is less than 20 degrees.

By generating the coaxial air stream A around the stagnant air that surrounds the spray plume, the vortices that are created are generally those based on the interaction of the surrounding, stagnant air and the coaxial air stream A. This aspect may help prevent smaller, lighter droplets (e.g., droplets broken up by vortices) from being carried away (rolled outward) by the vortices, thereby reducing and/or eliminating VOCs from drifting toward a user. Thus, the coaxial shield may prevent some or all of the blowback. Thus, the coaxial air stream A may confine some or all errant particles to the spray plume thereby reducing VOC emissions, while also increasing the droplet transfer efficiency. In some embodiments, the reduction of vortices and corresponding VOC emissions is optimal when the velocity of the coaxial air stream A is equal to the velocity of the droplets D exiting the spray nozzle 20. In some embodiments, the velocity of the coaxial air stream A is greater than the velocity of the droplets D exiting the spray nozzle 20.

In exemplary embodiments, the velocity of the pressurized air stream can be adjusted such that the velocity of the coaxial air stream A is equal to the velocity of the droplets D. For example, in some embodiments, a variable speed blower 40 can be disposed on the second end of the body 16. In some embodiments, the variable speed blower 40 may be located remote from the applicator 12 and the air may flow through a fluid tube (not shown) from the air source to the applicator 12. The speed of the blower 40 may be adjusted to increase or decrease the velocity of the pressurized air stream such that the velocity of the coaxial air stream A is equal to the velocity of the droplets D, e.g., by varying the input frequency and/or voltage of the blower. Yet, in other embodiments, the sprayer system can be configured so that the velocity of the coaxial air stream A and the velocity of the droplets D are set to be equal out of the box, e.g., via a default blower speed and/or nozzle orifice size and default fluid flow/pressure. In other embodiments, the velocity of the coaxial air stream A can be automatically adjusted, such as, for example, when employing a feedback loop for controlling the speed of the blower 40. In further embodiments, the velocity of the droplets D can be adjusted relative to the coaxial air stream A. For example, the velocity of the droplets can be adjusted increasing or decreasing the supply pressure, or varying the orifice size to generate a fluid velocity that matches the velocity of the coaxial air stream A.

In exemplary embodiments, generating a coaxial air stream A may increase the droplet transfer efficiency based on the lower portion of the coaxial air A stream formed underneath the spray plume D. Notably, the lower portion of the coaxial air stream A is particularly useful for carrying or projecting falling droplets (e.g., larger droplets falling via gravity) toward the target surface.

Still referring to FIG. 3, in some embodiments, the baffle 28 can optionally be formed to include a central channel 37 for receiving pressurized air generated by the blower 40. Air flowing through central channel 37 forms coaxial air stream B. The opening 37A of central channel 37 has a smaller cross-sectional volume than the outlet 38 of central channel 37, thus the air flow is reduced as it passes through central channel 37. Accordingly, the velocity of coaxial air stream B is lower than the volume of coaxial air stream A.

In such embodiments, pressurized air may enter the central channel 37 and exit through one or more openings 38 (FIG. 2) formed in the baffle 28, particularly, for aiding in projecting droplets D exiting the spray nozzle 20 toward the target surface.

Thus, in this exemplary embodiment, multiple coaxial air streams may surround or at least partially surround the spray plume of droplets D and aid in the transfer efficacy of the system. In this exemplary embodiment, one coaxial, or partially coaxial, air stream A may surround, or partially surround, the spray plume of droplets D, or two coaxial, or partially coaxial air streams A, B may surround, or partially surround, the spray plume of droplets D. In some embodiments, 3 or more coaxial air streams may surround, or partially surround, the spray plume of droplets D.

In some exemplary embodiments, the blower 40 can be configured to generate a pressurized air stream that flows through a cylindrical chamber 39 (FIG. 3) and diverges into the coaxial air stream A (via pressurized air entering the annular channel 36), and a coaxial air stream B (via pressurized air entering the central channel 37). In some embodiments, a cone (not shown) can be disposed upstream in the cylindrical chamber 39 to precondition the pressurized air stream for the divergence path.

Referring now to FIG. 2, in some embodiments, the optional radial fins 26 formed on the baffle 28 can be configured to serve as flow straighteners for creating a more directed and uniform airflow when the coaxial air stream A passes through the openings 38. Similarly, optional radial fins 32 may be configured to serve as flow straighteners for creating a more uniform air flow for optional coaxial air stream B. In this manner, the droplets conveyed by the pressurized air stream may be projected more uniformly toward the target surface.

Figure 4:
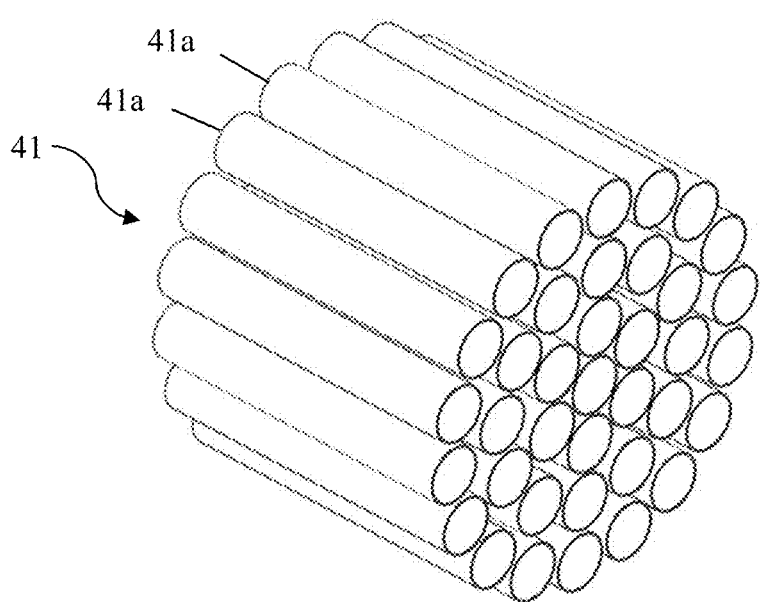
FIG. 4 illustrates a perspective view of a flow straightener for an applicator according to an exemplary embodiment.

Referring to FIGS. 3 and 4, the applicator 12 may also include a flow straightener 41 provided therein for eliminating, reducing, or at least partially reducing the swirling motion associated with the pressurized air generated by axial blower 40. In some embodiments, the flow straightener 41 may comprise an array of stacked tubes 41a (e.g., a honeycomb section) disposed in the cylindrical chamber 39. In such embodiments, each tube 41a comprises an air duct that is coaxial relative to the cylindrical chamber 39. Other types of air straighteners may be used, such as for example, elongated baffle members (not shown), elongated baffle members creating a plurality of square shaped passageways, rectangular shaped passageways, triangular shaped passageways, hexagonal shaped passageways, or other various geometric shaped passageways, or combinations thereof. In exemplary embodiments, conditioning the pressurized air stream via the flow straightener 41 may also increase the projected distance of the droplets D, respectively, based on a more directed and horizontal velocity component.

Figure 5:
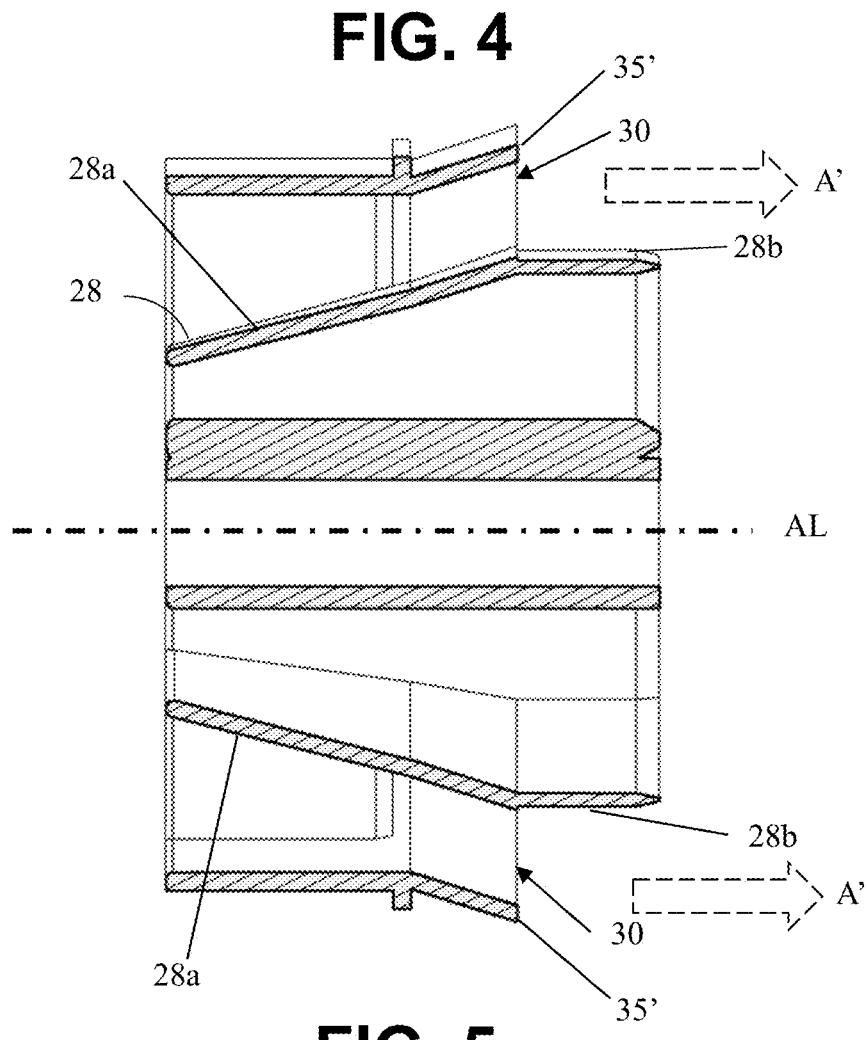
FIG. 5 illustrates a partial, cross-sectional view of an exemplary embodiment of a first end of the applicator of FIG. 2.

Still referring to FIG. 3, in some embodiments, an annular lip 35 may be formed along a circumferential periphery of the first end 14 of the applicator 12. In some embodiments, the annular lip 35 may extend outward such that the lip 35 is substantially horizontal and parallel to an outer circumferential wall 34 of the applicator 12. Yet, in other embodiments (e.g. FIG. 5), the annular lip 35' may be inclined, or flared outward, such that a distal end of the lip 35' is directed away from an axial line AL of the body. In exemplary embodiments, the annular lip 35 is configured to reduce vortices that would otherwise be created based on the interaction of the surrounding, stagnant air with the coaxial air stream A in the vicinity of the nozzle. In this manner, the annular lip 35 may be configured to help maintain the integrity of spray plume D such that the spray plume D is more focused as droplets are emitted from the spray nozzle 20. In some embodiments, the incline, or flare is adjustable. An adjustable incline or flare allows the device to be optimized for specific applications. While the illustrated embodiment of FIG. 3 depicts the annular lip 35 as having a distal end that is proximate the junction of the first and second portions 28a and 28b of the baffle 28, it should be appreciated that the annular lip 35 can be made longer, e.g., to extend past the spray nozzle 20. FIG. 5 shows annular lip 35' flared outward.

Figure 6:
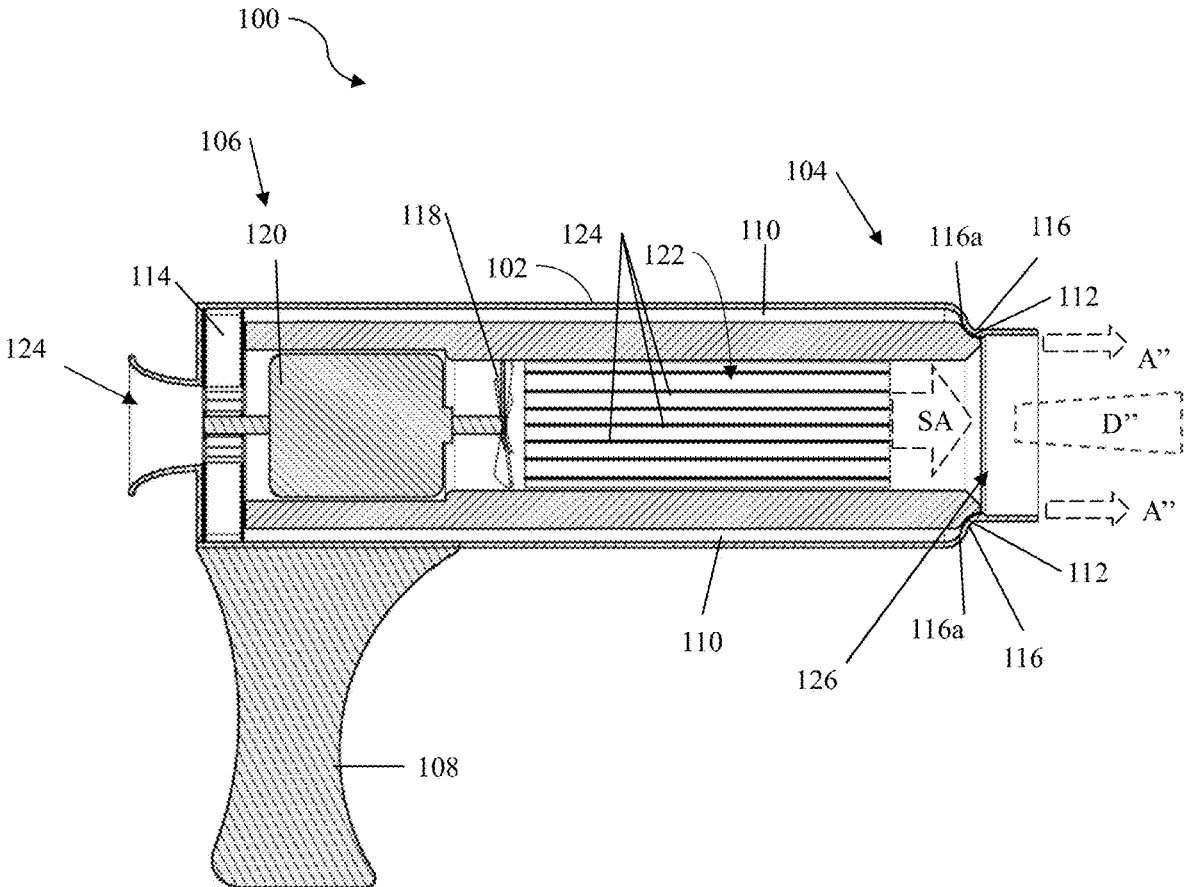
FIG. 6 illustrates a fine particle applicator according to another exemplary embodiment.

Referring to FIG. 6, another exemplary sprayer device/applicator 100 according to the present application is shown. Exemplary applicator 100 includes a body 102 having a first end 104 and a second end 106 with a handle 108 extending therefrom. A fluid line (not shown) is disposed in the body 102 for supplying pressurized fluid to a nozzle (not shown) that is configured to disperse the fluid into a spray plume of droplets D". The nozzle (not shown) can take any suitable form, such as, for example, any form of a nozzle described in the herein.

In this exemplary embodiment, an optional blower 114 (e.g., centrifugal blower) is disposed at the second end 106 for generating a first pressurized air stream through the annular channel 110. As the first pressurized air stream travels toward the first end 104, it encounters a baffle 116 having a convex-shaped, inner surface 116a. In particular, the inner surface 116a of the baffle 116 induces the pressurized air stream to pass over (or wrap around) the inner surface 116a and form a substantially, horizontal, coaxial air stream A' around the spray plume, e.g., via the Coanda effect, as discussed above. However, it should be understood that the configuration of the baffle 116 could take on multiple forms, such as, for example, any form of a baffle described in the present application, such as, for example, baffle 28 of FIGS. 2-5. In addition, in some embodiments, it should be appreciated that the first end 104 of the body 102 may also include an annular lip, such as, for example, annular lip 35 of FIGS. 3 and 5.

Still referring to FIG. 6, in some embodiments, the velocity of the first pressurized air stream can be adjusted such that the velocity of the coaxial air stream A" is equal to the velocity of the droplets. For example, in some embodiments, the blower 114 can embody a variable speed blower wherein the speed of the blower 114 can be adjusted to increase or decrease the velocity of the coaxial air stream A relative to the velocity of the droplets, e.g., by varying the input frequency and/or voltage of the blower. In some embodiments, one or more gears may be used to increase or decrease the rotational speed of the blower 114 with respect to the rotational speed of the motor 120 shaft. Yet, in other embodiments, the applicator 100 may be configured so that the velocity of the coaxial air stream A is equal to the velocity of the droplets, e.g., out of the box. In other embodiments, the velocity of the coaxial air stream A can be automatically adjusted, such as, for example, when a feedback loop is employed for controlling the speed of the blower 114. Yet, in other embodiments, the velocity of the droplets D can be managed to match the velocity of the coaxial air stream by adjusting the pressure or by utilizing a nozzle having a variable orifice size that generates a fluid velocity that matches the velocity of the coaxial air stream.

As discussed above, in some embodiments, the reduction of VOCs may be optimized when the velocity of the coaxial air stream A is equal to the velocity of the droplets D emitted from the nozzle. This feature may be particularly beneficial for preventing smaller, lighter droplets from being carried away by vortices, thereby reducing the possibility of VOCs from drifting toward a user. Moreover, and as discussed above, generating a coaxial air stream A also increases the droplet transfer efficiency based on the lower portion of the coaxial air stream A that is formed underneath the spray plume, e.g., for carrying or projecting falling droplets toward the target surface. In this manner, generating the coaxial air stream A may be especially useful for confining errant particles to the spray plume for reducing VOC emissions while also increasing the droplet transfer efficiency.

In some embodiments, the applicator 100 includes an optional axial blower 118 that is configured to generate a second pressurized air stream SA that helps project droplets exiting the nozzle toward the target surface, e.g., air assisted projection. In this exemplary embodiment, the second pressurized air stream SA passes through central channel 122 before reaching an opening 126 formed in the first end 104 of the applicator 100. In some embodiments, the second pressurized air stream SA flow is selected as a function of the amount of air volume and pressure that is required to help project the droplets toward the target surface, respectively, while also preserving the liquidity of the droplets as they reach the target surface. For seme embodiments that utilize an axial blower 118, the velocity of the second pressurized air stream SA can be adjusted to match the velocity of the droplets exiting the nozzle, e.g., by adjusting the voltage or input frequency of the blower 118, by adjusting the pitch of the blower blades, by adding one or more gears to the motor shaft, or the like. In some embodiments, the velocity of the droplets can be managed by applying the appropriate liquid pressure, or by utilizing a nozzle having an orifice size that generates a velocity that matches the velocity of the second pressurized air stream.

In some embodiments, motor 120 can be disposed in the second end 106 of the body 102 for driving the blower 114. Yet, in other embodiments, the motor 120 may be disposed between the blower 114 and the axial blower 118 for driving both the blower 118 and the blower 114. As discussed above one or more gears (not shown) may be included between the motor and the blower 114 and/or between the motor and the axial blower 118.

In some embodiments, a flow straightener 124 can be disposed in the central channel 122 to condition the second pressurized air stream SA by reducing swirling for creating a more directed and uniform air stream. In this manner, droplets conveyed by the second pressurized air stream SA may be projected more uniformly toward the target surface and with less mixing with the surrounding coaxial airstream and stagnant air, thus reducing VOC exposure for the operator. Conditioning the second pressurized air stream SA may also increase the projected distance of the droplets, based on a more directed, and horizontal velocity component. In exemplary embodiments, the flow straightener can take on any suitable form, such as, for example, elongated baffles. The elongated baffles may have circular cross-sectional shapes, rectangular cross-sectional shapes, square cross-sectional shapes, triangular cross-sectional shapes, other geometrical cross-sectional shapes, and/or combinations thereof.

Figure 7:
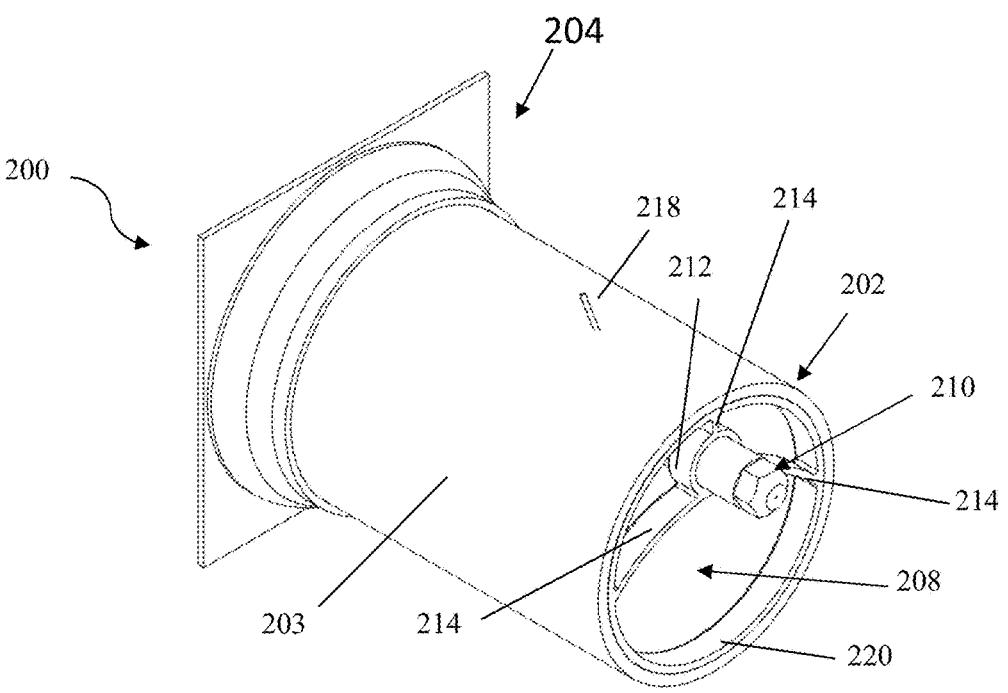
FIG. 7 illustrates a perspective view of a applicator according to another exemplary embodiment.
Figure 8:
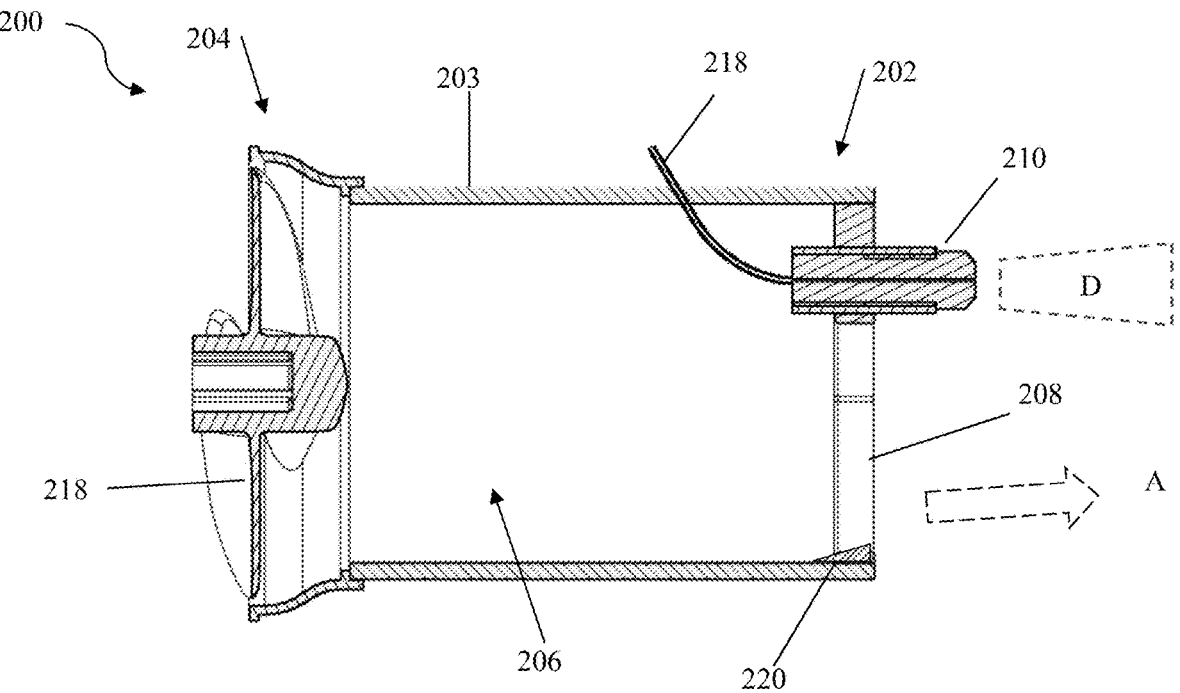
FIG. 8 illustrates a cross-sectional view of the applicator of FIG. 7.

Referring now to FIGS. 7 and 8, another exemplary embodiment of an applicator 200 is shown. There may be additional components that are not shown in this illustration for simplicities sake, such as, for example, a handle, a connection port for supplying liquid, a power source, electronics needed for controlling one or more of the electrical devices, and the like. Exemplary applicator 200 includes a first end 202, a second end 204, and a channel 206 that is formed therein. In exemplary embodiments, a lower opening 208 is formed into the first end 202 to serve as an outlet for pressurized air. In this exemplary embodiment, a nozzle 210 is located above and proximate the lower opening 208. The nozzle 210 is received in receiving hub 212 that is connected to a circumferential wall 203 of the applicator 200 via one or more support arms 214. Areas between support arms 214 may be filled in to prevent air flow therebetween. For example, the two areas between the three support arms 214 may be filled in, thereby restricting air flow through channel 206 to exit below nozzle 210.

In exemplary embodiments, the nozzle 210 is configured to disperse pressurized fluid supplied by a fluid line 218 into a spray plume of droplets D (FIG. 8). The nozzle 210 can take any suitable form, such as, for example, any form of a nozzle described in the instant application. While the fluid line 218 is shown as passing through the circumferential wall 203 of the body, it should be appreciated that other configurations are also contemplated, e.g., can pass through a rear portion of the body, or through a handle (not shown) and into the body.

In some exemplary embodiments, a blower 218 is disposed at the second end 204 of the applicator 200 for generating a pressurized air stream that passes through the channel 206 and exits the applicator 200 through the lower opening 208. As the pressurized air stream exits the lower opening 208, it encounters a lip 220 that is formed along a periphery of the lower opening 208. In some embodiments, the lip 220 is inclined upward such that the height of the lip 220 gradually increases in the direction of first end 202.

More specifically, in some embodiments, the lip 220 can be optionally configured to direct the pressurized air stream A underneath a spray plume of droplets D exiting the nozzle 210. In some embodiments, the lip 220 aids in increasing the droplet transfer efficiency by carrying or projecting falling droplets (such as, for example, larger droplets falling via gravity) toward the target surface. More specifically, droplets falling under gravity in this embodiment would enter the core of the pressurized air stream A and be effectively carried to the target surface. In some embodiments, incorporating a slight angle of inclination into the lip 220 produces a modest upward vector that helps counter the gravity drop of larger droplets emitted from the nozzle 210. In some embodiments, lip 220 is adjustable so the device may be optimized for a specific application. In some embodiments, the pressurized air stream A generated by the blower 218 is directed below the nozzle with minimal air flow above and to the sides of the nozzle. Preferably, the majority of the pressurized air stream A does not intermix with the droplets D, thereby helping preserve the liquidity of the droplets as they reach the target surface. As discussed above, this aspect may also help increase a droplet's dwell time on the target surface for more effectively disinfecting germs that exist on the target surface.

In some embodiments, the velocity of the pressurized air stream can be adjusted relative to the velocity of the droplets, such as, for example, by any suitable means of adjusting air or fluid velocity described in the present application, e.g., voltage adjustment, automatic adjustment, preset velocity, liquid pressure, via the nozzle orifice size, etc.

In some embodiments, a flow straightener (not shown) can be disposed in the applicator 200 to condition the pressurized air stream as it passes through the channel 206 to reduce swirling and to provide a more directed and uniform air stream. As described above, the flow straightener (not shown) can take any suitable form. In some embodiments, the lip 220 can be contoured to reduce vortices and VOC emissions that would otherwise be created based on the interaction of the surrounding, stagnant air with the spray plume near an upper portion of the applicator 200. Moreover, forming a lip may also stabilize VOC carrying eddies formed in the vicinity of the nozzle.

Figure 9:
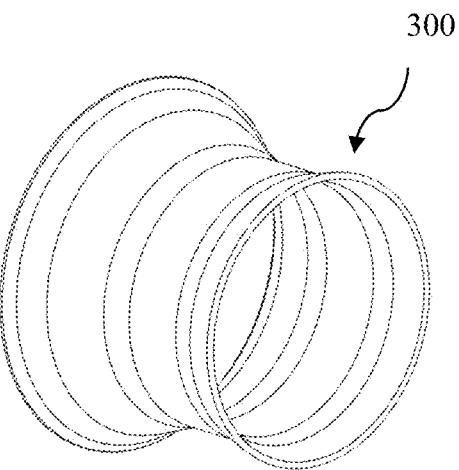
FIG. 9 illustrates a perspective view of an exemplary applicator shroud.
Figure 10:
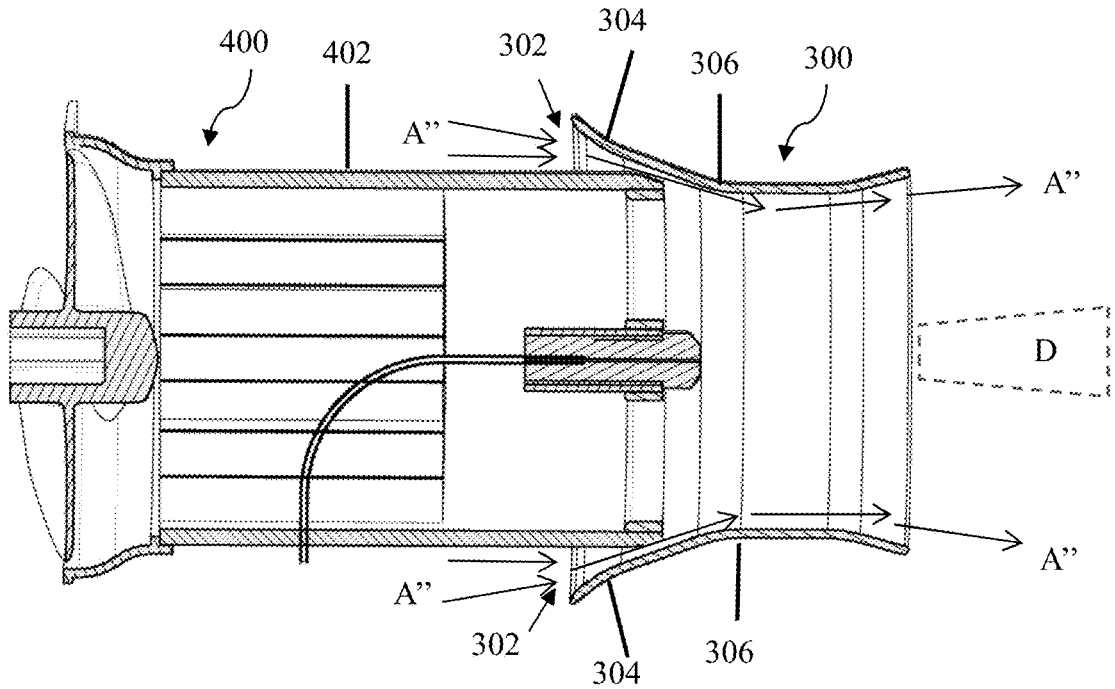
FIG. 10 illustrates a cross-sectional view of the applicator shroud of FIG. 9 attached to an applicator.

Referring now to FIG. 9, an exemplary shroud 300 is shown. Exemplary shroud 300 may be sized and dimensioned to be removably attached to a first end of an applicator (see, e.g., 400 of FIG. 10). In some embodiments, the shroud 300 may be integrally formed on the body 400. In some embodiments, the shroud 300 is configured to create an air sleeve A" around the spray plume by passively inducting air through a circumferential air duct 302 that is defined by the space between an arcuate-shaped wall 304 of the shroud 300 and the adjacent, circumferential wall 402 of the body 400. As depicted in FIG. 10, air traveling through the air duct 302 wraps around an inner surface of the arcuate-shaped wall 304 via the Coanda effect, to form a substantially, horizontal circumferential air barrier A" around the spray plume. The air barrier A" that is created by the shroud is particularly useful for stabilizing eddies formed in the vicinity of the nozzle. More specifically, the shroud 300 may prevent errant particles from being swept away via eddies, thereby reducing VOCs that are directed toward a user.

Referring now to FIGS. 11-13, an exemplary sprayer system 500 is shown. Exemplary sprayer system 500 includes an applicator 502, a blower 504, and a housing 506. Referring to FIG. 13, in exemplary embodiments, the applicator 502 includes a handle or any grip method 507 extending therefrom or otherwise part of, and a nozzle 505 that is disposed at a first or front end 503 of the applicator 502. In exemplary embodiments, the nozzle 505 is configured to disperse pressurized fluid into droplets and direct the droplets toward a target surface. As shown in FIG. 11, in some embodiments, the applicator 502 is connected to a housing 506 via a utility line 508. The utility line 508 comprises a fluid line that is configured to supply a liquid disinfectant from the housing 506 to the applicator 502. Yet, in other embodiments, the utility line 508 may comprise a fluid conduit and/or a power cable and/or an air conduit, as discussed in greater detail below. In exemplary embodiments, the housing 506 may include a reservoir 507 for storing a liquid disinfectant, and a pump (not shown) that is configured to drive the liquid disinfect ("pressurized fluid") from the reservoir to the applicator 502 via the fluid line.

Referring to FIG. 13, in exemplary embodiments, a blower 504 may be attached to the applicator 502. More specifically, in some embodiments, the blower 504 may be removably attached to a lower portion of the front end 503 of the applicator 502, e.g., via retention clips, resilient snaps, or any other suitable attachment means. In such embodiments, the blower 504 may establish an electrical connection with the applicator 502 when it is attached to the applicator 502. In this manner, the blower 504 will receive power via a power cable that is disposed in the utility line 504 that is connected to the applicator 502. In such embodiments, the housing 506 may include a power supply that can provide power to the pump and to the blower, e.g., to the blower via the power cable in the utility line 504. In exemplary embodiments, the blower is a 120 mm square frame blower capable of generating a 60 cubic feet per minute (ft³/min.) air flow rate. However, it should be appreciated that other configurations of a blower 504 are also contemplated. In exemplary embodiments, the blower 504 is configured to generate a lower air stream A underneath a spray plume D of droplets exiting the nozzle 505, respectively, for lifting errant droplets (e.g., larger droplets falling via gravity) back into the spray plume. In this way, the air stream A that is generated by blower 504 improves the droplet transfer efficiency by lifting and carrying errant and/or falling droplets toward the target surface, e.g., droplets that lacked sufficient kinetic energy to make it to the target surface. This feature is particularly suitable for improving the droplet transfer efficiency and preventing droplets from falling to the ground surface and creating a slipping hazard. For example, in some embodiments, the droplet transfer efficiency may be improved by 20-50% at a distance of 18-36 inches from a vertical, target surface. Moreover, to directing the air stream A underneath the spray plume helps circumvent droplets D from intermixing with the air for preserving the liquidity of the droplets as they reach the target surface. This aspect also helps increase a droplet's dwell time, as discussed in detail above.

In some embodiments, the velocity of the air stream that is generated by the blower can be adjusted so that it is equal to the velocity of the droplets, as discussed in detail above, e.g., via blower speed control, liquid pressure control, nozzle orifice size, etc. In this manner, the reduction of VOCs can be optimized based on a reduction of vortices at the interface between the droplets D and the air stream A.

Referring to FIG. 14, in some embodiments, the blower 504 may be removably attached to the housing 506 when operating the applicator 502 without the blower 504, e.g., for applications that are closer in proximity to the target surface. In some embodiments, the blower 504 may also be made available to retrofit existing, commercially available sprayers, e.g., as an aftermarket accessory for improving droplet transfer efficiency. Moreover, in some embodiments, the housing 506 can be configured to receive replaceable fluid containers that may be sold as a replacement items, e.g., containers of liquid disinfectant that can be received by the housing 506 for quick, product replenishment purposes. In some embodiments, an extender wand (not shown) can be removably attached to a rear portion of the applicator 502 to space the operator from a first end of the sprayer for further reducing face-level exposure to VOC emissions.

In some embodiments, the applicator 502 may be releasably detachable to the housing 506. Thus, the applicator may be held in one hand for spraying operation as shown in FIG. 11 or it may be secured to the housing and operated as shown in FIG. 14.

The fine droplet sprayer for spraying a disinfectant onto a surface may comprises a first air moving device for moving air through the first air passage and a second air moving device for moving air through the second air passage.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. It is not the intention of the applicant to restrict or in any way limit the scope of the appended claims to such detail. Unless expressly excluded herein, all such combinations and sub-combinations are intended to be within the scope of the present inventions. Still further, while various alternative embodiments as to the various aspects, concepts and features of the inventions—such as alternative materials, structures, configurations, methods, circuits, devices and components, software, hardware, control logic, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order in which the steps are presented to be construed as required or necessary unless expressly so stated.

We claim:

1. A fine droplet sprayer for spraying a disinfectant onto a surface, comprising:
   a reservoir for holding a disinfectant fluid;
   a pump for pumping the disinfectant fluid;

16 an applicator;
   a fluid dispensation conduit extending from the pump to the applicator;
   the applicator having;
      a housing;
      a liquid outlet nozzle;
      an air moving device configured to blow or pump air;
      a first air passageway from the air moving device to a first air outlet;
      wherein the first air outlet is at least partially cylindrical;
      wherein air flowing from the air moving device to the first air outlet forms at least a partial cylindrical air stream;
      wherein the at least a partial cylindrical air stream exits the first air outlet at a first speed;
      wherein the at least partial cylindrical air stream is located around a periphery of the housing;
      wherein the at least partial cylindrical air stream is located away from the liquid outlet nozzle, such that the at least partial cylindrical air stream does not contact the fluid at the time the fluid is pumped out of the liquid outlet nozzle;
   further comprising a second air passageway having a second air outlet,
      wherein the air moving device directly moves a second airstream out of the second air outlet;
      wherein the second air stream enters a second air inlet;
      wherein the second air outlet has a larger cross-sectional area than the second air inlet; and
      wherein the second air outlet is located between the first air outlet and the liquid outlet nozzle.

2. The fine droplet sprayer for spraying a disinfectant onto a surface of claim 1 wherein the housing is cylindrical.

3. The fine droplet sprayer for spraying a disinfectant onto a surface of claim 1 wherein the at least a partial cylindrical air stream is located below the fluid as the fluid is pumped out of the liquid outlet nozzle.

4. The fine droplet sprayer for spraying a disinfectant onto a surface of claim 1 further comprising a baffle, wherein the baffle narrows the cross-sectional area of the first air passageway in the direction of flow and cause air flowing through the first air passageway to accelerate.

5. The fine droplet sprayer for spraying a disinfectant onto a surface of claim 1 wherein a baffle is configured to cause a Coanda effect on the first air.

6. The fine droplet sprayer for spraying a disinfectant onto a surface of claim 2 further comprising a baffle, wherein the baffle expands the cross-sectional area of the second air passageway in the direction of flow and cause air flowing through the second air passageway to decelerate.

7. The fine droplet sprayer for spraying a disinfectant onto a surface of claim 1 further comprising baffles for conditioning air flowing therethrough to reduce air turbulence, wherein the baffles extend longitudinally along a fluid flow path.

8. The fine droplet sprayer for spraying a disinfectant onto a surface of claim 1 wherein the air moving device comprises a first air moving device for moving air through the first air passage and a second air moving device for moving air through the second air passage.

* * * * *